United States Patent [19]

Fukushima et al.

[11] Patent Number: 4,720,335

[45] Date of Patent: Jan. 19, 1988

[54] WIDE RANGE AIR FUEL RATIO SENSOR

[75] Inventors: Megumu Fukushima; Kasunari Komatsu; Yasuhiro Shidahara; Katihiro Yokomizo, all of Hiroshima, Japan

[73] Assignee: Mazda Motor Corporation, Japan

[21] Appl. No.: 898,821

[22] Filed: Aug. 18, 1986

Related U.S. Application Data

[62] Continuation of Ser. No. 727,538, Apr. 26, 1987, abandoned, which is a continuation-in-part of Ser. No. 553,254, Nov. 18, 1983, abandoned.

[30] Foreign Application Priority Data

Dec. 1, 1982 [JP] Japan .................. 57-210998

[51] Int. Cl.$^4$ ........................................ G01N 27/46
[52] U.S. Cl. ............................ 204/424; 204/1 T; 204/291; 204/292; 204/421; 204/427; 427/404; 427/419.2
[58] Field of Search ............ 204/1 S, 421–429, 204/291, 292; 427/419.2, 404

[56] References Cited

U.S. PATENT DOCUMENTS

| | | | |
|---|---|---|---|
| 3,481,855 | 12/1969 | Kolodney et al. | 204/422 |
| 3,914,169 | 10/1975 | Horowitz | 204/427 |
| 3,989,614 | 11/1976 | Tien | 204/427 |
| 4,021,326 | 5/1977 | Pollner et al. | 204/429 |
| 4,040,929 | 8/1977 | Bauer | 204/426 |
| 4,097,353 | 6/1978 | Kishida et al. | 204/429 |
| 4,514,277 | 4/1985 | Sakurai et al. | 204/424 |

*Primary Examiner*—T. Tung
*Attorney, Agent, or Firm*—Gerald J. Ferguson, Jr.; Michael P. Hoffman; Michael J. Foycik, Jr.

[57] ABSTRACT

An air-fuel ratio sensor for detecting the air-fuel ratio in intake gas introduced into an engine by way of the oxygen concentration in engine exhaust comprises an oxygen ion transmissive solid electrolyte body and first and second porous electrodes provided on opposite sides of the solid electrolyte body, the first porous electrode being adapted to be brought into contact with the exhaust. The first porous electrode is formed of a material which exhibits semi-catalytic property. Metal oxide which oxidizes HC to produce CO is provided near three-phase points at which said first electrode, the solid electrolyte body and the exhaust adjoin each other when the first electrode is brought into contact with the exhaust.

4 Claims, 10 Drawing Figures

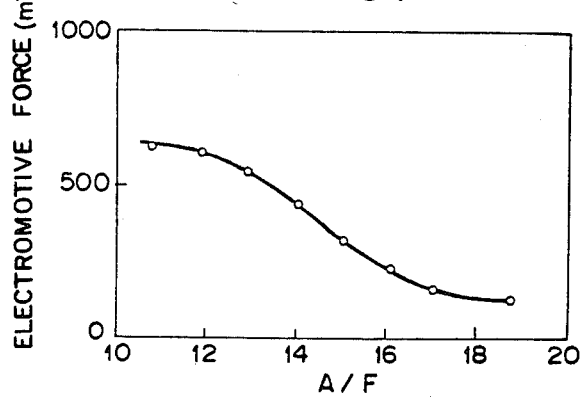

WIDE RANGE AIR FUEL RATIO SENSOR

CROSS-REFERENCES TO RELATED APPLICATIONS

This application is a continuation of Ser. No. 727,538, filed Apr. 26, 1985, now abandoned, which is a continuation-in-part, of Ser. No. 553,254, filed Nov. 18, 1983, now abandoned.

BACKGROUND OF THE INVENTION

1. Field of the Invention

This invention relates to a wide-range air-fuel ratio sensor for an engine, and more particularly to a wide range air-fuel ratio sensor for detecting the air-fuel ratio in intake gas introduced into the engine by way of the oxygen concentration in the engine exhaust.

2. Description of the Prior Art

As is well known in the art, the air-fuel ratio in the intake gas introduced into a vehicle engine, for example, can be detected by detecting the oxygen concentration in the engine exhaust. As the detector for detecting the oxygen concentration in the exhaust, there has been known a so-called λ sensor whose electromotive force changes stepwise when the value of the oxygen concentration varies across the value corresponding to the stoichiometric air-fuel ratio. The λ sensor cannot accurately measure individual values of the air-fuel ratio deviating from the stoichiometric value though it can detect whether the actual air-fuel ratio in the intake gas introduced into the engine is larger or smaller than the stoichiometric value.

In vehicles, when the engine is to operate at high power, e.g., when the vehicle is operating under high load or is accelerated, it is preferred that the intake gas be rich, i.e. that the air-fuel ratio be smaller than the stoichiometric value. On the other hand, when the vehicle is cruising at a steady high speed, it is preferred that the intake gas be lean, i.e. that the air-fuel ratio be larger than the stoichiometric value in order to reduce fuel consumption. In order to control the air-fuel ratio to a value different from the stoichiometric value, the actual air-fuel ratio must be accurately detected, and accordingly the λ sensor, which can only detect whether the actual air-fuel ratio is larger or smaller than the stoichiometric value, cannot be used for this purpose.

In Japanese Unexamined Patent Publication No. 57(1982)-76450 and Japanese Patent Publication No. 53(1978)-34077, there have been proposed oxygen concentration detecting devices which can measure individual values of the oxygen concentration. These oxygen concentration detecting devices are both directed to improving said λ sensor which comprises a solid electrolyte body bearing a pair of porous electrodes on opposite sides thereof. The one disclosed in the former publication is a so-called amperometric sensor in which a protective layer is provided on the outer surface of the electrode to be brought into contact with sample gas, to control diffusion of the gas toward the electrode. On the other hand, in the one disclosed in the latter publication, the porous electrodes are poisoned to lower their sensitivity to gradually reduce the overall electromotive force characteristics thereby obtaining linear electromotive force characteristics. However, in both the oxygen concentration detecting devices, linear electromotive force characteristics can be obtained only in the rich region, i.e., the region in which the actual air-fuel ratio is smaller than the stoichiometric air-fuel ratio. Further, the width of the region in which the electromotive force characteristics are linear is narrow; for instance, from 100 to 200 mV, and therefore, the detecting sensitivity of the devices is insufficient for practical use.

SUMMARY OF THE INVENTION

In view of the foregoing observations and description, the primary object of the present invention is to provide a wide-range air-fuel ratio sensor which can measure individual values of the air-fuel ratio over a wide range from the lean region to the rich region and which has high sensitivity sufficient for practical use.

The wide-range air-fuel ratio sensor of the present invention comprises a solid electrolyte body, first and second porous electrodes provided on opposite sides of the solid electrolyte body, the first electrode being brought into contact with engine exhaust and being formed of a material exhibiting "semi-catalytic property", and a metal oxide which is adapted to oxidize HC (hydrocarbon) to produce CO and is disposed near a three-phase point at which the first electrode, the solid electrolyte body and the exhaust adjoin each other.

DETAILED DESCRIPTION OF THE INVENTION

The term "semi-catalytic property" used in this specification will be explained first.

Figure 1:
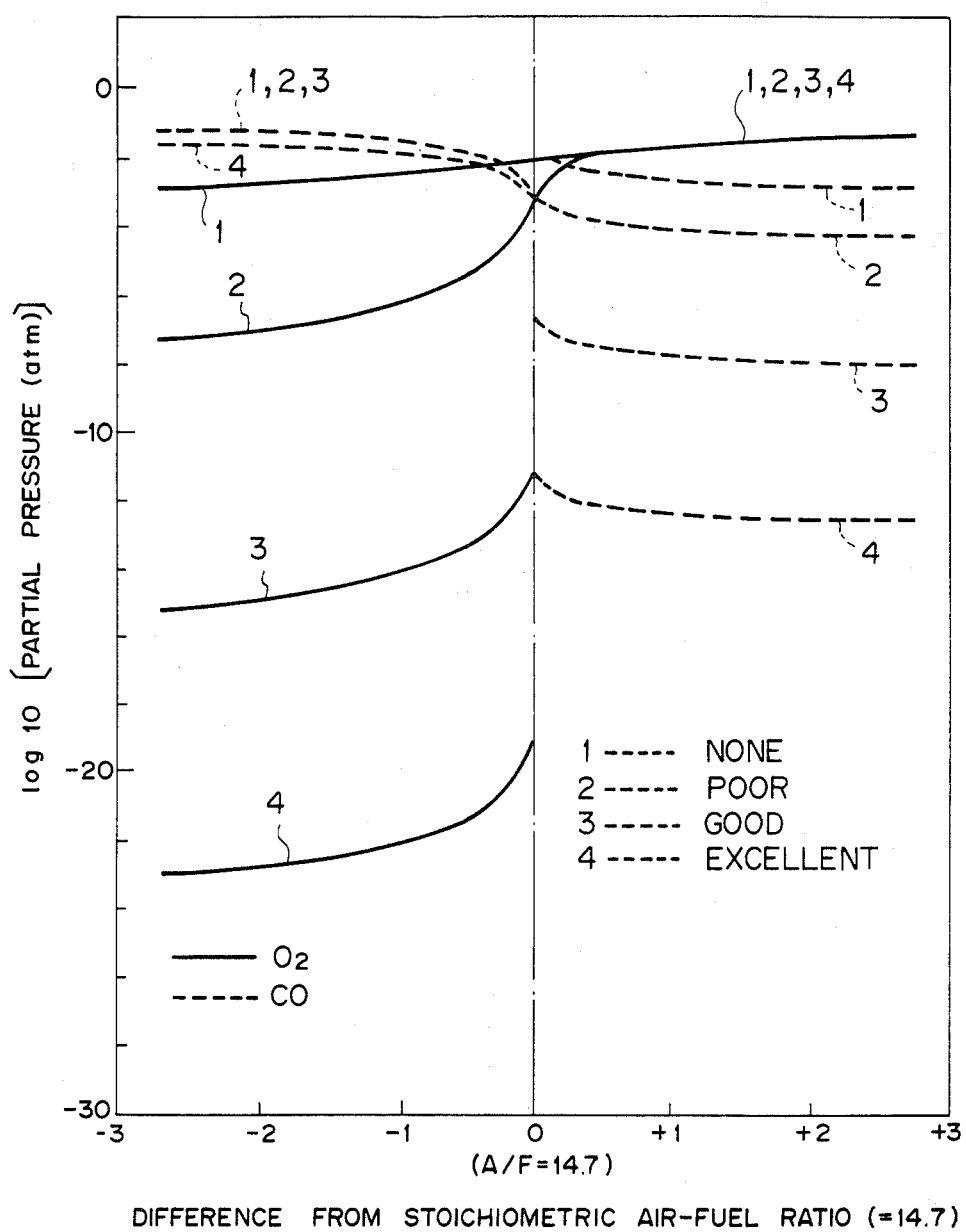
FIG. 1 is a graph showing changes in partial pressure of $O_2$ and CO at the three-phase point according to electrode catalytic activity.

FIG. 1 is a graph showing changes in partial pressure of $O_2$ and CO at the three phase point according to electrode catalytic activity, which was taken from a paper by William J. Fleming entitled "Physical Principles Governing Nonideal Behavior of the Zirconia Oxygen Sensor", published in Electrochemical Society, Vol. 124, No. 1, pp. 21–28, January 1977. In FIG. 1, the catalytic activity is classified into first (none), second (poor), third (good) and fourth (excellent) degrees. The term "semi-catalytic property" denotes a property of exhibiting activity not higher than the second degree. Typically, silver and gold exhibit the semi-catalytic property. Though being regarded as of high activity and having been used in the conventional λ sensor, platinum can exhibit semi-catalytic property depending on firing conditions and raw material.

Figure 2:
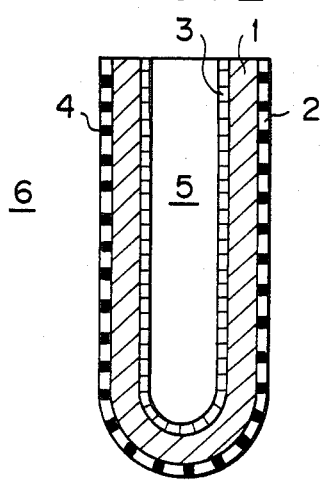
FIG. 2 is a schematic cross-sectional view of a wide-range air-fuel ratio sensor in accordance with an embodiment of the present invention.
Figure 3:
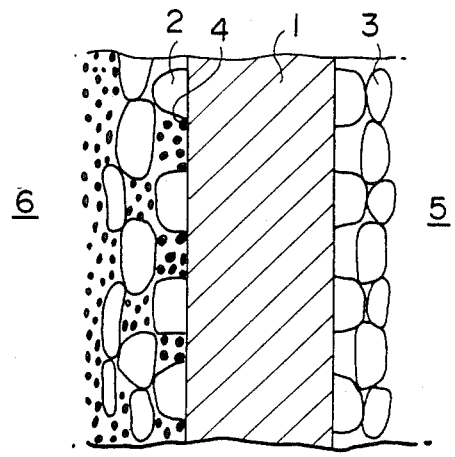
FIG. 3 is an enlarged fragmentary view of FIG. 2.
Figure 4:
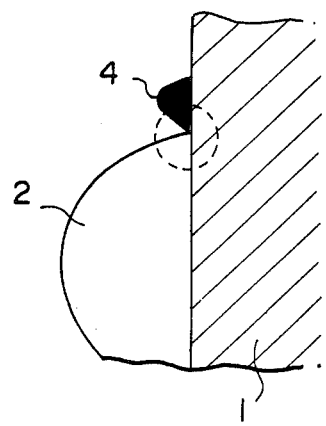
FIG. 4 is a further enlarged fragmentary view of FIG. 3.

FIG. 2 shows a wide-range air-fuel ratio sensor in accordance with an embodiment of the present invention. The sensor of this embodiment comprises a tubular solid electrolyte body 1, a first porous electrode 2 provided on the outer side of the solid electrolyte body 1 and a second porous electrode 3 provided on the inner side of the same. The first porous electrode 2 is brought into contact with exhaust 6 with the second porous electrode 3 being in contact with the atmosphere 5. A layer of metal oxide 4 is formed over the first porous electrode 2 so that the metal oxide 4 exists near three-phase points at which the solid electrolyte body 1, the first porous electrode 2 and the exhaust 6 adjoin each other as shown in FIGS. 3 and 4. A typical three-phase point is shown encircled by a dotted line in FIG. 4. The first porous electrode 2 is made of material exhibiting semi-catalytic property and the metal oxide 4 is selected from materials able to oxidize HC to produce CO.

Now the mechanism by which linear electromotive force characteristics are obtained with respect to the air-fuel ratio will be explained in detail.

Figure 5A:
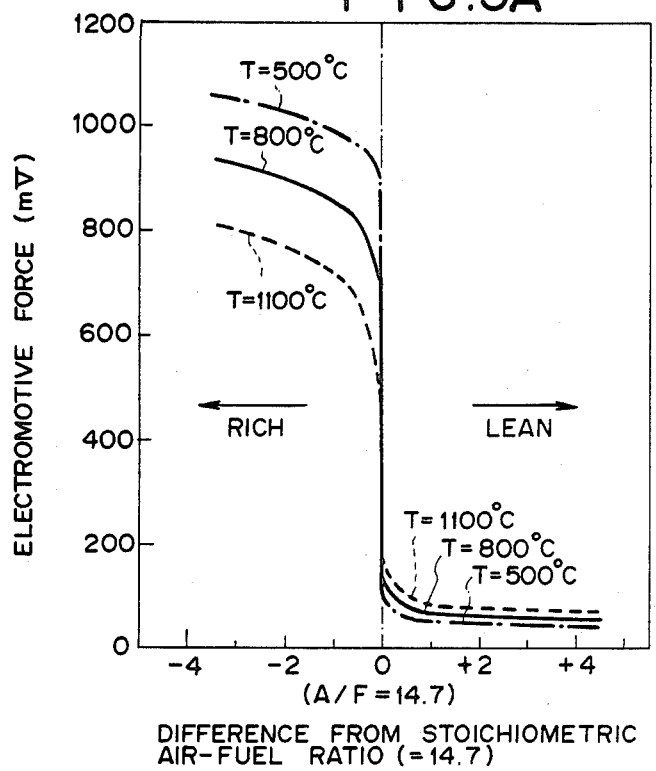
FIG. 5A is a graph showing the relation between the air-fuel ratio and the electromotive force of an ideal sensor for several temperatures of sample gas.

As is well known, the electromotive force V of an ideal sensor is given by the Nernst equation:

$$V = (RT/4F)\ln[P_{O2}(air)/P_{O2}(exh)]$$

wherein R represents the gas constant, T represents the absolute temperature, F represents Faraday constant, Po2(air) represents the partial pressure of oxygen in the atmosphere and Po2(exh) represents the partial pressure of oxygen in the exhaust. When the electrode in contact with the exhaust has such a high catalytic activity as to cause the gas to attain equilibrium, an electromotive force characteristic curve like those shown in FIG. 5A can be obtained by plotting values derived from the equation. Actually, however, most sensors exhibit electromotive force characteristics which cannot be accounted for by the Nernst equation. Thus, William J. Fleming has proposed an equivalent circuit model. The behavior of the wide-range air-fuel ratio sensor of the present invention can be accounted for by Fleming's equivalent circuit model.

Fleming's equivalent circuit model is based on the fact that electromotive force specific to each adsorption point is generated at each three-phase point, and the electromotive force V is given by the following equation:

$$V = f_{co} \cdot V_{co} + (1 - f_{co})V_{o2}$$

wherein $f_{co}$ represents the proportion of the three-phase points on which CO is adsorbed, $V_{co}$ represents the electromotive force generated at the three-phase point on which CO is adsorbed and $V_{o2}$ represents the electromotive force generated at the three-phase point on which $O_2$ is adsorbed, and $f_{co}$, $V_{co}$ and $V_{o2}$ are respectively given by the following equations:

$$f_{co} = K_{co} \cdot P_{co}/(1 + K_{co} \cdot P_{co} + K_{o2} \cdot P_{o2})$$

wherein Kco and Ko2 respectively represent the adsorption constants of CO and $O_2$; and $$V_{co} = V°_{co} + (RT/2F)\ln[P_{O2}^{\frac{1}{2}}(air) \cdot P_{co}(anode)/P_{co2}(anode)]$$

$$V_{o2} = V°_{o2} + (RT/4F)\ln[P_{O2}(air)/P_{O2}(anode)]$$

wherein $V°_{co}$ and $V°_{o2}$ represents the standard cell potentials of the respective electrochemical cells, and Pcocanode), Pco2(anode) and Po2(anode) respectively represent the partial pressures of CO, $CO_2$ and $O_2$ at the three-phase point on the electrode in contact with the exhaust. The above equations are derived from the following two reactions at the three-phase point.

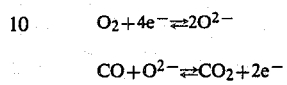

$$CO + O^{2-} \rightleftharpoons CO_2 + 2e^-$$

The difference in electromotive force characteristics between the actual sensor and the ideal sensor is mainly due to the fact that the catalytic performance of the cathode is insufficient. That is, the electromotive force substantially depends upon the difference between the partial pressures of CO and $O_2$ at the three-phase point. As can be seen from FIG. 1, in the lean region, the partial pressure of $O_2$ is substantially constant independent of the catalytic activity while the partial pressure of CO changes by a large amount depending upon the catalytic activity. Accordingly, the electromotive force in the lean region mainly depends upon the partial pressure of CO. Thus, according to Fleming's equation, the electromotive force can be increased by increaasing the partial pressure of CO in the lean region.

Taking into account the conditions described above, description will be made hereinbelow about the mechanism by which linear electromotive force characteristics can be obtained in accordance with the present invention.

Said metal oxide acts as an oxidizing catalyst which oxidizes HC in the exhaust to produce CO with itself being reduced. For example, when $SnO_2$ is used as the metal oxide, the following reaction occurs:

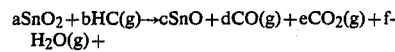

The resulting SnO is oxidized by $O_2$ in the exhaust to return to $SnO_2$. That is, $SnO_2$ repeats production of CO and absorption of $O_2$ by so-called redox reactions:

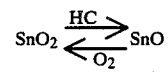

Figure 5B:
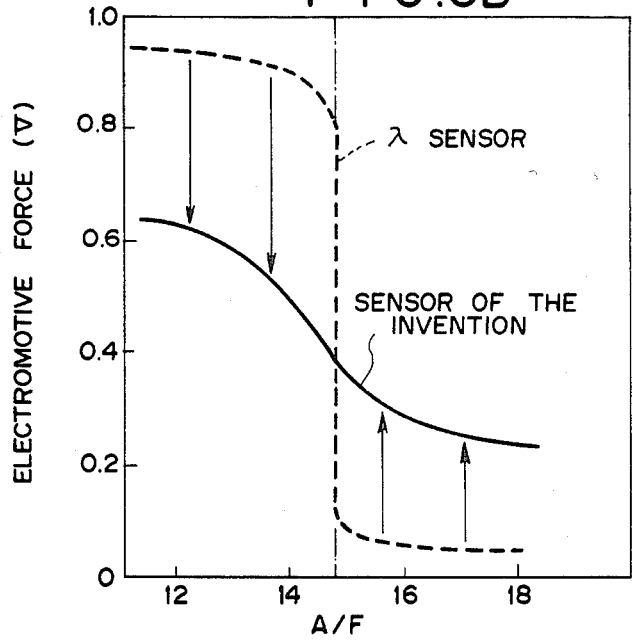
FIG. 5B is a view illustrating the electromotive force characteristics of the wide-range sensor of the present invention as compared with those of the conventional λ sensor, FIGS. 6 and 7 respectively show microscopic views of an electrode comprising Pt before and after exposure to engine exhaust, FIGS. 8 and 9 respectively show the relation between the electromotive force and the air-fuel ratio in the wide-range air-fuel ratio sensors obtained by examples 1 and 2.

Thus the partial pressure of $O_2$ is lowered and the CO produced from HC raises the partial presure of CO near the three-phase points and accordingly the electromotive force in the lean region is increased as shown in FIG. 5B, whereby substantially linear electromotive force characteristics can be obtained in the lean region.

Further, because the porous electrode in contact with the exhaust, i.e., the first porous electrode, has semi-catalytic property in accordance with the present invention, the electromotive force in the rich region is lowered as shown in FIG. 5B, whereby substantially linear electromotive force characteristics can be obtained over a wide range extending from the lean region to rich region.

The HC concentration in the lean region only amounts to from several hundreds to a thousand ppm at most. Accordingly, only a very little amount of CO is produced by the metal oxide. However, when the relevant CO is generated near the three-phase points and can reach these before being oxidized by the surface of the porous electrode, the partial pressure of CO is changed from the value designated by the curve corresponding to the catalytic activity of the fourth degree to the same designated by the curve corresponding to the catalytic activity of the second degree even if the concentration of the relevant CO is as small as 0.001%. This is the reason why the metal oxide must exist near the three-phase point in accordance with the present invention.

As can be understood from the description above, the metal oxide should have high HC-oxidizing power. The HC-oxidizing power or the CO-producing power of various metal oxides can be analogized from Table 4.10 "Propylene Oxidizing Reaction on Various Metal Oxides" in "Metal Oxides and Their Catalytic Effect" by Tetsuro Kiyoyama published by Kodansha, p. 185, 1979, for example. For example, when the porous electrode to be brought into contact with the exhaust (the first porous electrode 2) is formed of a material containing Pt as the major component, e.g., platinum paste, $SnO_2$, $In_2O_3$, NiO, $CO_3O_4$ and CuO exhibit sufficient HC-oxidizing power. That is, when the first porous electrode 2 is formed of a material containing Pt as the major component, the metal oxide may be one or more of the above identified metal oxides. Because production of CO by oxidizing HC is affected by the total balance of the catalytic activity of the first porous electrode and the HC-oxidizing power of the metal oxide, when the first porous electrode is formed of a material containing, as the major component, a material having lower catalytic activity than Pt, e.g., Ag or Au, other metal oxides having lower HC-oxidizing power than the above metal oxides can be used. For example, when the first porous electrode 2 is formed of Ag paste, ZnO and $MnO_2$ may be used as the metal oxide 4.

On the other hand, material having higher activity than the metal oxides, e.g., precious metals such as Pt and Rh, cannot be used in place of the metal oxides, because such highly active materials tend to oxidize HC into $CO_2$ and $H_2O$ and produce little CO, and at the same time oxidize CO in the exhaust into $CO_2$, thereby lowering the partial pressure of CO at the three-phase point.

Figure 6:
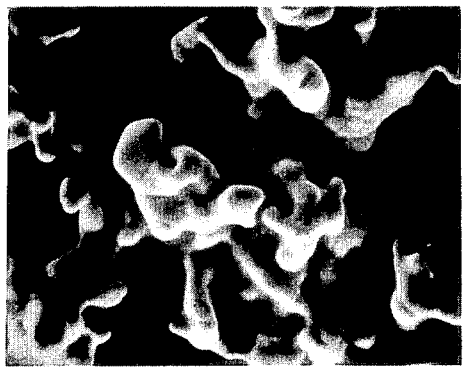
Figure 7:
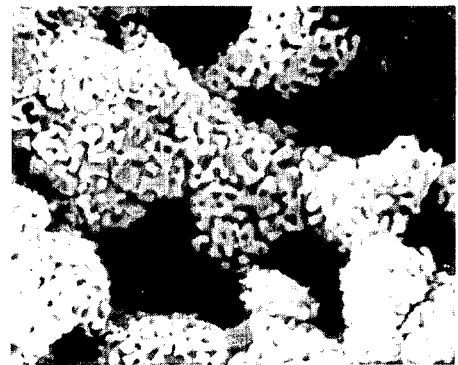

Further, such materials having high catalytic activity as Pt obtained by thermal decomposition of $(NH_4)_2[PtCl_6]$ which has been used in the λ sensor as the porous electrodes cannot be used as the first porous electrode 2 in the present invention, because when the first porous electrode 2 is formed of materials having high catalytic activity, most HC and CO are oxidized by the first porous electrode 2 and no HC can exist near the three-phase point, whereby production of CO by the metal oxide 4 is prevented. Further, in order to obtain mild electromotive force characteristics in the rich region, the first porous electrode must exhibit said semi-catalytic property. Pt, Au and Ag have sufficiently low resistance so as to be used as a material for the electrode. When the electrode comprising Pt is exposed to engine exhaust for a long period of time, it becomes porous due to a known reaction between Pt and C. That is, C is fused into Pt at a high temperature and then deposited thereon at a low temperature, thereby forming pores therein. Thus, the microstructure of the electrode would change, for example, from one shown in FIG. 6 to one shown in FIG. 7 after a long exposure to the exhaust. Accordingly, the surface area of the electrode becomes large thus increasing its catalytic activity. On account of the foregoing, its initial linear electromotive force characteristics would be lost.

Though the sensitivity (gradient of output against the air-fuel ratio) of the sensor using Au or Ag as the electrode lower than one using Pt, the former is superior to the latter in durability because the aforesaid reaction between C and Pt, which may modify the catalytic property, does not occur in the former.

Now, examples of the present invention will be described hereinbelow.

EXAMPLE 1

A wide-range air-fuel ratio sensor having the structure shown in FIG. 2 was made by the following procedure. A tubular solid electrolyte body 1 was formed of a solid electrolyte material consisting of $ZrO_2$ containing 8 mol% of $Y_2O_3$ (available from Nihon-Kagaku-Togyo). Pt paste was coated on the inner side of the solid electrolyte body 1 by brushing, dried at 120° C., and then fired for one hour at 1050° C. in an electric oven, whereby the second porous electrode 3 having a thickness of 15μ was formed on the inner side of the solid electrolyte body 1. Au paste was coated on the outer side of the solid electrolyte body 1, dried at 120° C., and then fired for 15 minutes at 850° C. in an electric oven, whereby the first porous electrode 2 was formed on the outer side the solid electrolyte body 1. The solid electrolyte body 1 bearing thereon the first and second porous electrodes 2 and 3 thus obtained was dipped into a suspension prepared by mixing together $SnO_2$ having a controlled particle size of not larger than 5μ, ethyl silicate condensate and ethyl alcohol in the ratio of 3:1:1, thereby impregnating the suspension into pores of the first porous electrode 2, and then air-dried. It was further heated and fired for 30 minutes at 800° C. in an electric oven so that $SnO_2$ was entrapped near the three-phase spot.

Figure 8:
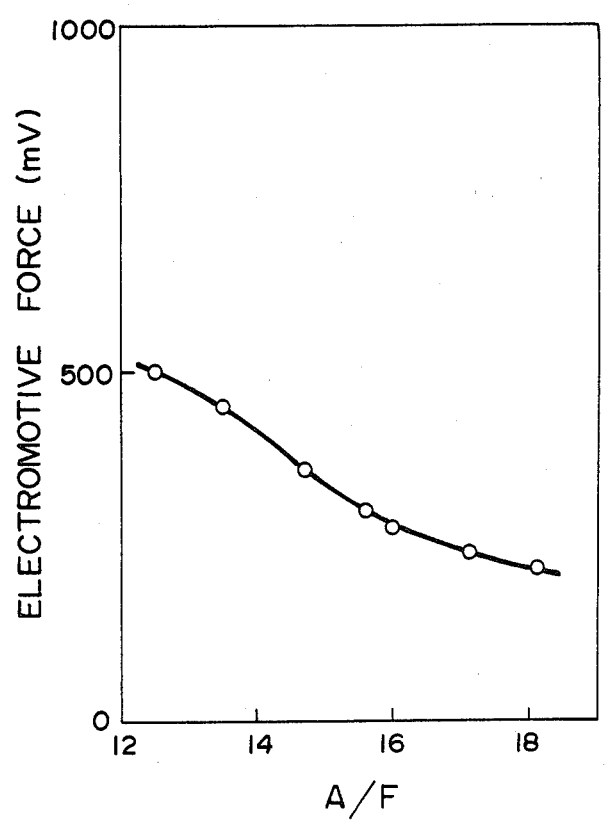

The wide-range air-fuel ratio sensor in accordance with the first embodiment of the present invention thus obtained was incorporated into the exhaust system of a reciprocating engine and was subjected to a bench test. In the test the electromotive force was measured while the air-fuel ratio was changed from 12 to 18 with the temperature of the exhaust in the region near the sensor being maintained at 600° C. The sensor exhibited linear electromotive force characteristics as shown in FIG. 8.

EXAMPLE 2

A wide-range air-fuel ratio sensor having the structure shown in FIG. 2 was made by the following procedure. A tubular solid electrolyte body 1 was formed of a solid electrolyte material consisting of $ZrO_2$ containing 8 mol% of $Y_2O_3$ (available from Nihon-Kagaku-Togyo). Ag paste (silver past MH4511 available from Tanaka-Massei) was coated on opposite sides of the solid electrolyte body 1 by brushing, dried at 120° C., and then fired for one hour at 650° C. in an electric oven, whereby first and second porous electrodes 2 and 3 were formed on the solid electrolyte body 1. The thickness of each porous electrode was 10μ. The solid electrolyte body 1 bearing thereon the first and second porous electrodes 2 and 3 thus obtained was dipped into a suspension prepared by mixing together $MnO_2$ having controlled particle size of not larger than 3μ and ethyl silicate condensate in the weight ratio of 3:2, thereby impregnating the suspension into pores of the first porous electrodes 2, and then air-dried. It was further heated and fired for 30 minutes at 600° C. in an electric oven so that $MnO_2$ was entrapped near the three-phase point.

The wide-range air-fuel ratio sensor in accordance with the second embodiment of the present invention thus obtained was incorporated into the exhaust system of a reciprocating engine and was subjected to a bench test. In the test the electromotive force was measured while the air-fuel ratio was changed from 11 to 19 with the temperature of the exhaust in the region near the sensor being maintained at 600° C. The sensor exhibited electromotive force characteristics as shown in FIG. 9.

What is claimed is:

1. A wide-range air-fuel ratio potentiometric sensor for detecting the air-fuel ratio in intake gas introduced into an engine by way of the oxygen and HC concentration in engine exhaust, prepared by providing, drying, and firing an electrode material formed of at least one of Ag and Au on a solid electrolyte body to thereby respectively form porous electrodes on the opposite sides of the solid electrolyte body where one of said porous electrodes is in contact with the engine exhaust and both porous electrodes on opposite sides of the solid electrolyte body are electrically isolated from any external source of electrical potential, an electromotive force being generated between the porous electrodes, and the electromotive force being a function of the partial pressures of $O_2$ and CO at a three phase point at which the solid electrolyte, the exhaust side porous electrode, and the exhaust adjoin each other, and impregnating, drying, and firing a metal oxide, for oxidizing said HC to CO, in the pores of the exhaust side porous electrode to provide sufficient metal oxide for oxidizing HC to CO near said three-phase point at which the solid electrolyte, the exhaust side porous electrode, and the exhaust adjoin each other where the amount of said metal oxide present in said exhaust side porous electrode is such that a substantial gradient in said electromotive force exists for a range of values of the air-fuel ratio extending from about the stoichiometric value of 14.7 to values substantially geeater than the stoichiometric value and where the amount of said Au or Ag in said first porous electrode with respect to said metal oxide is such that the gradient of said electromotive force is substantially linear for values of the air-fuel ratio substantially less than said stoichiometric value.

2. A wide-range air-fuel ratio sensor as defined in claim 1 in which said metal oxide is at least one of $SnO_2$, $In_2O_3$, NiO, $Co_3O_4$ and CuO.

3. A wide-range air-fuel ratio sensor as defined in claim 1 in which said metal oxide is at least one of ZnO and $MnO_2$.

4. A wide-range air-fuel ratio sensor as defined in claim 1 in which said metal oxide is $MnO_2$.

* * * * *